United States Patent [19]

Rast

[11] Patent Number: 4,940,891
[45] Date of Patent: Jul. 10, 1990

[54] AUTOMATED SYSTEM FOR MEASURING THE STRENGTH OF OPTICAL FIBERS

[75] Inventor: Howard E. Rast, Solana Beach, Calif.

[73] Assignee: The United States of America as represented by the Secretary of the Navy, Washington, D.C.

[21] Appl. No.: 397,074

[22] Filed: Aug. 22, 1989

[51] Int. Cl.$^5$ .............................................. H01J 5/16
[52] U.S. Cl. ............................... 250/227.15; 356/73.1
[58] Field of Search .................... 250/227.15; 356/73.1

[56] References Cited

U.S. PATENT DOCUMENTS 4,636,638  1/1987  Huang ............................ 250/227.15

OTHER PUBLICATIONS

"Fiber Strength Assurance for Deep Submarine Optical Fiber Cable Using the Proof-Testing Method", *Journal of Lightwave Technology*.
"Simultaneous Multilevel Proof Testing of High Strength Silica Fiber", *Electronics Letters*.
"Military Systems Requirements for Strong Optical Fibers", *SPIE Guided Wave Optical & Surface Acoustic Wave Devices, Systems and Applications*.
"Failure Prediction for Long Length Optical Fiber Based on Proof Testing", *Journal of Applied Physics*.
"Liquid Nitrogen Strengths of Coated Optical Glass Fibers", *Journal of Materials Science* (1980).
"A Bending Method for Measurement of the Tensile Strength and Young's Modulus of Glass Fibers", *Journal of Applied Physics*.
"Statistical Reproducibility of the Crack Propagation Parameter N in Dynamic Fatigue Tests", *J. Am. Ceramic Soc.* 62.

*Primary Examiner*—David C. Nelms
*Assistant Examiner*—Sherrie Hsia
*Attorney, Agent, or Firm*—Harvey Fendelman; Thomas Glenn Keough

[57] ABSTRACT

A system automatically measures the strength of optical fibers by initiating a series of breaks in an optical fiber delivered from a supply spool. The fiber is stressed to failure in an automatically displacable jaw mechanism and the fiber is advanced and the measurement repeated. A computer-controller advances the fiber, records data and monitors jaw mechanism fracture parameters so that the strength distribution of a length of optical fiber is reliably determined.

8 Claims, 3 Drawing Sheets

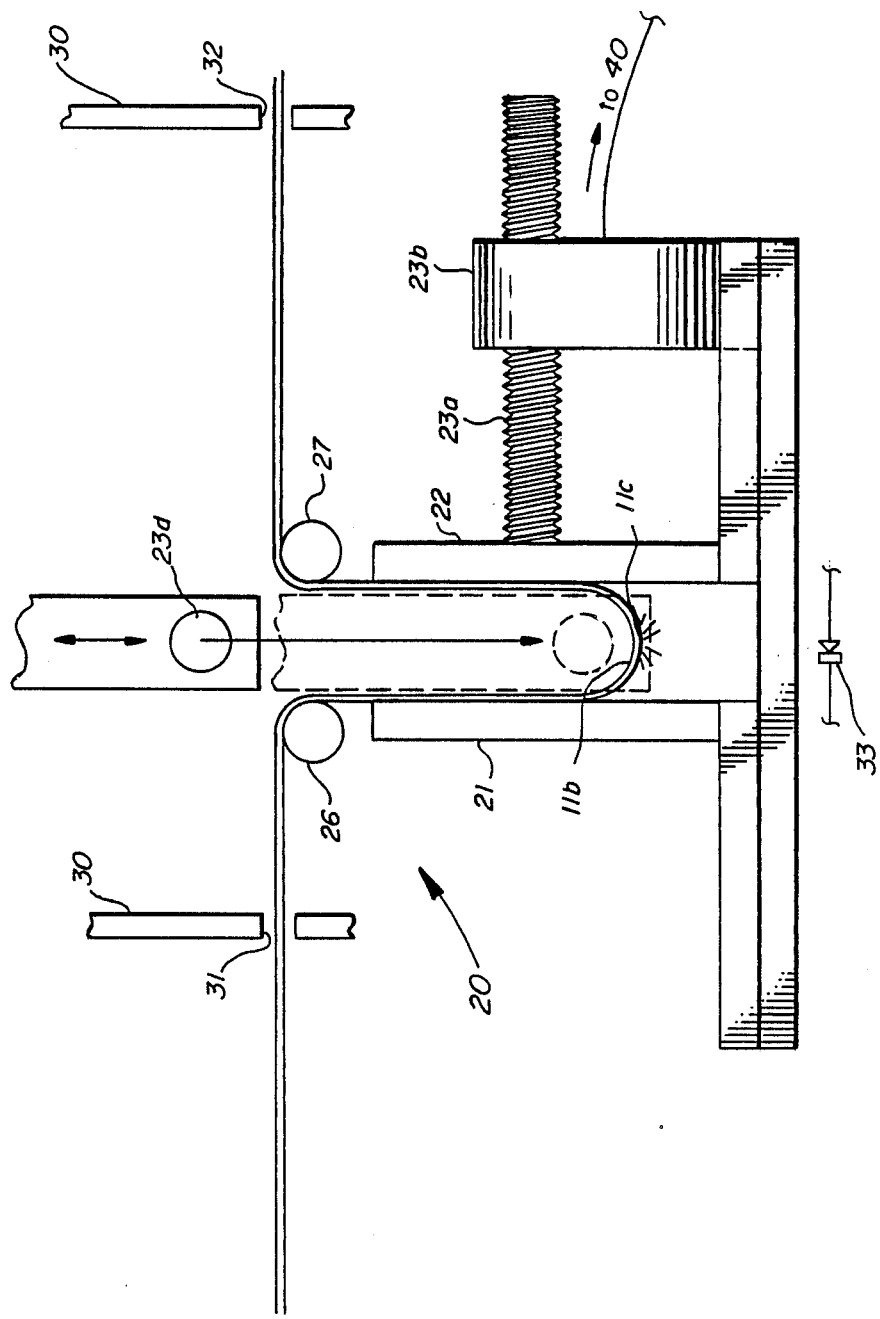

AUTOMATED SYSTEM FOR MEASURING THE STRENGTH OF OPTICAL FIBERS

STATEMENT OF GOVERNMENT INTEREST

The invention described herein may be manufactured and used by or for the Government of the United States of America for governmental purposes without the payment of any royalties thereon or therefor.

BACKGROUND OF THE INVENTION

Several methods of measuring the strength distribution of optical fibers have been developed over the years. One known as the dynamic test method relies upon the random selection of a series of lengths, $L_0$, of fiber from a longer length, L. The fibers are tested to failure in a tensile test machine by applying a constant loading rate $\dot{\sigma}$. The stress $\sigma_f$ at which the fiber fails then is recorded. A plurality of these lengths, $L_0$, called the gauge length, is measured to provide a statistical sample of size D, usually D is greater than or equal to 30. The data are then ordered in a series ranging from lowest strength to highest and assigned an approximate failure probability $F_i(\sigma)$ where $$F_i = i/D + 1 = 1 - exp\{-(\sigma_{fi}\sigma_p/\sigma_o - \sigma_p)\}^M \quad (1)$$

In this equation $\sigma_{fi}$ is the failure stress of the i-th sample, $\sigma_p$ is a proof-stress if the fiber was previously proof tested, $\sigma_o$ is a constant and M, the exponent, is constant for a given environment. Graphical plots of the function of equation (1) enable the assignment of an average strength to the fiber length L because the length $L_0$ is related to the strength of the length L by the relation, $S_L = S_{Lo} exp\ \theta\ (-L/L_0)$.

Another method of measuring strength distributions is by means of static fatigue testing. In this method the fiber is not subjected to a changing rate of stress but rather a constant loading by a weight W and the time to failure is measured. A variation of this is to wind the length $L_0$ on mandrels of varying diameters and measure the time-to-failure of breaks in the fiber. The stress of failure is given by the expression $$\sigma_{fs} = approx.\ E(\rho/R_F) \quad (2)$$

where E is Young's modulus, $\rho$ the radius of the fiber and $R_F$ is the radius of the mandrel. The relation between time-to-failure under static and dynamic conditions is approximately given by the relationship $$t_d(\sigma_d^N) = (N+1)\ (t_s)\ \sigma_s^N. \quad (3)$$

where $t_d$ and $t_s$ are the respective dynamic and static times to failure and $\sigma_d$ and $\sigma_s$ are the dynamic and static stresses at failure. The constant N, sometimes called the fatigue parameter, occurs in several known theories of the fracture mechanics of ceramics. It is a measure of the tendency of the material to suffer stress corrosion and relates various fracture mechanic parameters to the velocity of crack propagation preceding from flaws under stress. The disadvantage of these measurement techniques is that they are slow, tedious and require a great deal of handling of the fiber, selecting samples and applying the various techniques for measuring time-to-failure).

David Sinclair of the Johns-Manville Research Center discloses a method for measuring strength in his article entitled "A Bending Method For Measurement of the Tensile Strength and Young's Modulus of Glass Fibers" appearing in the *Journal of Applied Physics*, volume 21, May 1950, pg. 380 et seq.. Mr. Sinclair discusses a bending method which consists of twisting a loop of fiber, pulling the ends until the loop breaks and measuring the force. While the procedure seemed to produce accurate representations of fiber strength, the number of discrete operations necessary to perform the step-by-step procedure had the appearances of being labor intensive and time consuming. Another technique was disclosed by P. W. France et al in their article entitled "Liquid Nitrogen Strengths of Coated Optical Glass Fibers" in the *Journal of Materials Science*, 15 (1980), pgs. 325 et seq.. They relied on a man-actuated U-shaped bender for receiving a fiber and stressing it until it breaks for the purposes of determining indications of tensile strength. Here again, the results were found to be satisfactory yet it appeared that a considerable number of manipulations of the fiber and device might make this procedure a bit time consuming and labor intensive.

Thus, there is a continuing need in the state of the art for an automated system for measuring the strength of optical fibers that is consistent to provide acceptable indications of strength yet which does not call for a labor-intensive and time consuming procedure.

SUMMARY OF THE INVENTION

The present invention is directed to providing an apparatus and method for rapidly and automatically measuring the strength distribution in an optical fiber. A laser or other suitable light source is optically coupled to the optical fiber for projecting light longitudinally through the fiber's core. A light sensing device is disposed adjacent the optical fiber, preferably in a light-tight, absorptive enclosure for sensing light emanating from breaks in portions of the optical fiber. An automated jaw mechanism is disposed to receive the optical fiber for initiating a number of breaks of the fiber as the optical fiber is fed therethrough by a motor driven supply spool and a take up reel. A suitable switching device, such as a computer controller, is operably connected to the light sensor, the supply spool, the take up reel and the jaw mechanism for actuating the automatic feeding of portions of the optical fiber to the jaw mechanism by the rotation of the supply spool and the take up reel and initiating the separate breaking of sequential portions of the optical fiber in the jaw mechanism to provide a series of breaks in the optical fiber along its length in response to the sensing of light emanating from each of the breaks in the fiber. The jaw mechanism, working in sequential cooperation with the supply spool, the take up reel and the sensing device, is sequentially reciprocated to create the series of breaks by automatically bending the portions of the fiber into separate u-shaped bends in the optical fiber and compressing them into tighter hairpin-shaped configurations until the fiber breaks. When each break occurs, the light emanates (scatters from radiation modes) and is sensed by the sensor to cause the withdrawal of the jaw mechanism from its converged position so that another portion of the optical fiber can be repositioned for another break sequence.

A prime object of the invention is to provide an automated system for rapidly measuring the strength of optical fibers.

Another object is to provide an optical fiber strength measuring device which needs little operator interface to perform a series of strength tests.

Another object is to provide an optical fiber strength measuring device that relies upon optically sensing breaks in the fiber to initiate repositioning of the fiber for initiating another break sequence.

A further object of the invention is to provide an apparatus to efficiently streamline strength measurements without having to cut samples, insert them in a tensile test machine and manually collect strength and failure data.

Still another object is to provide an apparatus to interface with a computer-controller to realize a complete data acquisition system for determining the strength of an optical fiber.

Yet another object is to provide an apparatus for testing optical fiber strength that makes use of light guiding and scattering on breakage to provide a means to exactly determine loop diameter at breakage.

These and other objects of the invention will become more readily apparent from the ensuing specification and drawings when taken in conjunction with the attached claims.

BRIEF DESCRIPTION OF THE DRAWINGS

FIG. 3 is a schematic side view of the jaw mechanism to assure an automated system for measuring a fiber's strength.

DESCRIPTION OF THE PREFERRED EMBODIMENTS

Figure 1:
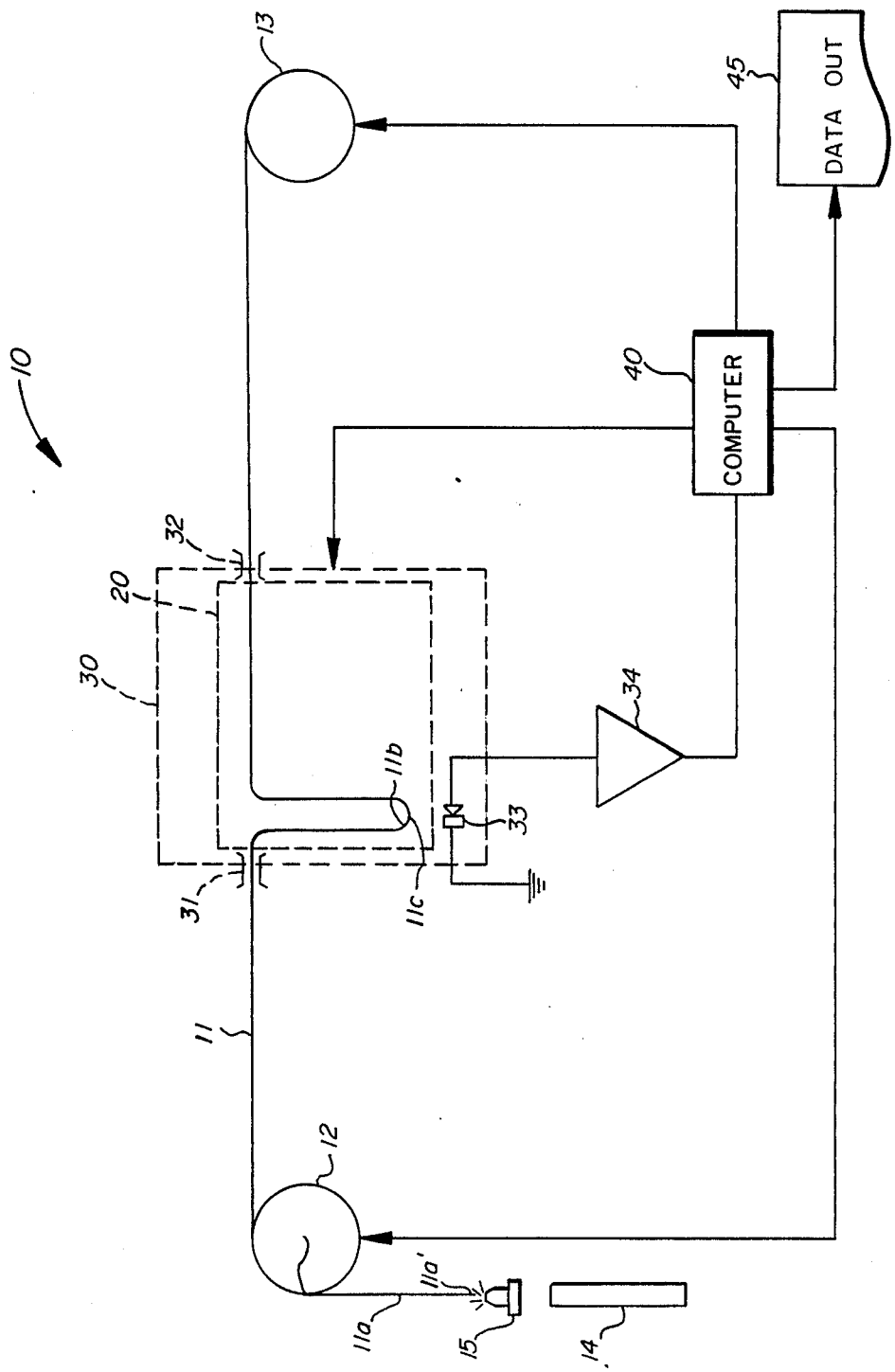
FIG. 1 shows a schematic representation of the principle constituents of this invention.

The invention introduces the capability for accurately and automatically determining the strength distribution of an optical fiber 11, see FIG. 1. This is accomplished by the apparatus to be described by measuring the diameter of a loop of optical fiber 11 when it is bent into a U-shape 11b to such an extent that it breaks 11c. In accordance with predetermined measurements the failure diameter $d_1$ is measured when the core of the fiber is fractured and a particular fiber is said to fail. The stress at failure, $\sigma_f$ is approximately equal to the relationship $$\sigma_f = 2 E (\rho/d_1)$$

where E is Young's modulus for silica, $\rho$ is the radius of the silica fiber and $d_1$ is the diameter of U-shaped loop 11b at failure.

Referring now to FIG. 1 of the drawings an optical fiber strength distribution testing system 10 allows the rapid and automatic measuring of the strength distribution in an optical fiber 11. The optical fiber is coiled on a motor-driven storage drum 12 and fed to a motor-driven take-up reel 13. Drum 12 has a length 11a of optical fiber integrally extending from optical fiber 11 to assure an optical coupling. The drum and reel are actuated appropriately in a controlled fashion to be elaborated on below to sequentially feed predetermined portions of the optical fiber to other parts of the system.

A high intensity light source 14, such as a helium-neon laser, is focused via an appropriate coupler 15 into a launch end 11a' of length 11a of the optical fiber. Thus, high intensity light travels the length of optical fiber where the illuminated fiber passes through a jaw mechanism 20.

Figure 2:
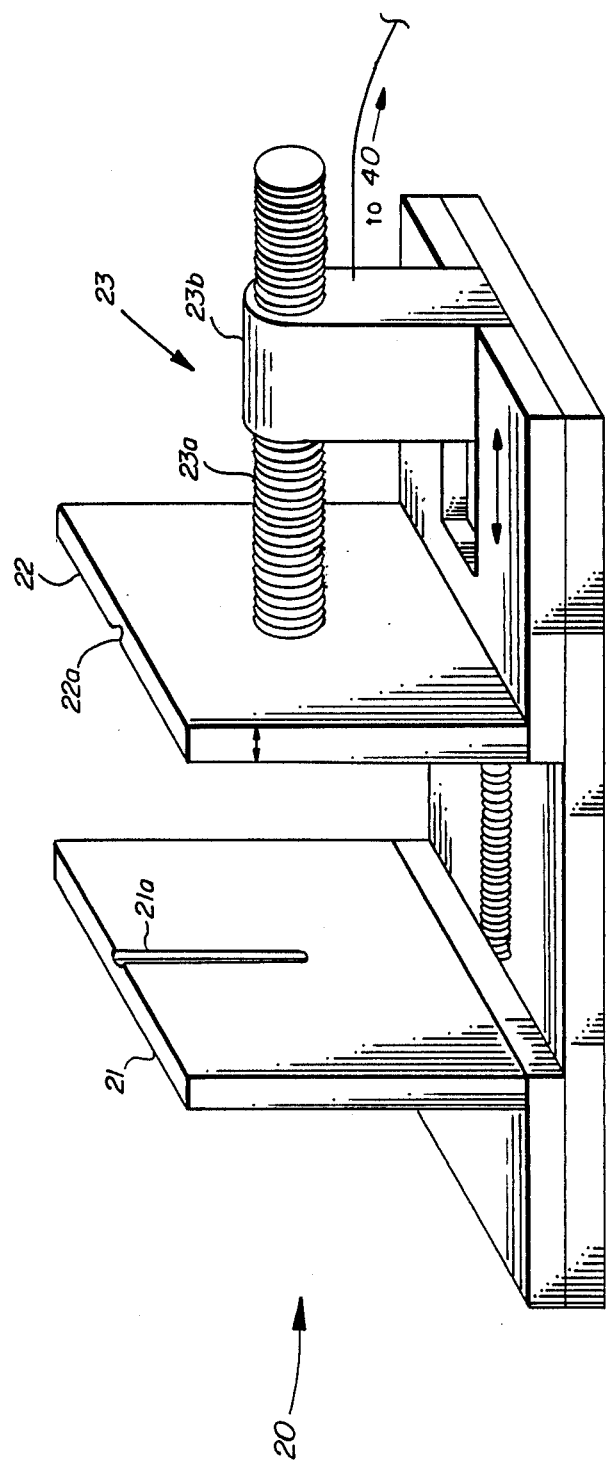
FIG. 2 is an isometric depiction of the jaw mechanism of this invention.

The jaw mechanism is at least partially contained within a light absorbing enclosure 30 and its function is to automatically impart a series of determinable separate U-shaped bends in optical fiber 11 in a manner to be described in greater particularity with respect to FIGS. 2 and 3. The enclosure is sufficiently sized to contain the portion of optical fiber 11 that includes each U-shaped portion 11b and is provided with a pair of small openings 31 and 32 that permit the in and out passage of optical fiber 11.

A light sensing device 33, such as a photo detector, is mounted in light-tight and absorptive enclosure 30 and is coupled to an amplifier 34. The light sensor provides signals representative of when light breaks occur at 11c as a portion of optical fiber 11 is bent into a U-shape configuration 11b that is less than the fiber's core break diameter. Where the breaks occur, light sensor 33 senses the light emanating from the fiber and provides a responsive signal for amplification at amplifier 34.

A sensing of light emanating from a break 11c in optical fiber 11 by sensor 33 generates a signal for a controller 40 to transfer predetermined appropriate signals for motor-driven drum 12 to pay out more optical fiber 11 and for motor-driven take up reel 13 to reel in a predetermined portion of optical fiber 11. Controller 40 also transfers predetermined appropriate signals to jaw mechanism 20 to open and receive a sequential portion of optical fiber 11 for the beginning of another break sequence and to a suitable transcribing or recording device 45 for the recording of data.

The controller may be a suitably programmed micro chip or commercially available computer w/ A-D converter or flip-flops suitably programmed to automatically tally, sort, order and process data to compute strength parameters and appropriately actuate the elements mentioned immediately above. Fabrication and interconnection of such a controller is well within the capabilities of one skilled in the art to which this invention pertains. All that is involved is the passing of appropriate signal levels in a clearly discernable switching sequence upon the receipt of a light pulse signal of a suitable level from amplifier 34. As such, further elaboration on the details of the controller is dispensed with at this time to avoid belaboring the obvious.

Noting once again FIGS. 1, 2 and 3, fiber 11 is fed from motor-driven supply spool 12 and it enters and leaves light-tight enclosure 30 via openings 31 and 32. Jaw mechanism 20 shapes fiber 11 into a U-shaped loop 11b between a stationary L-shaped block 21 and a moveable L-shaped block 22. Each of the L-shaped blocks is provided with a smooth groove 21a and 22a respectively to receive and retain fiber 11, see FIG. 2.

A motor-drive stage 23 of jaw mechanism 20 has a screw 23a displaced by a stepping motor 23b and a solenoid or motor-driven roller bearing 23d, The stepping motor and roller bearing are selectively controlled by the appropriate signals coming from controller 40.

Screw 23a is appropriately coupled to moveable L-block 22 to selectably move it toward or away from stationary L-block 21 and cause a controlled variation of the diameter of loop 11a as the moveable L-block approaches or recedes from the stationary L-block. In accordance with control signals coming from controller 40, when the moveable block selectably is displaced toward the stationary block, the size of the loop of 11b is diminished to reach the critical diameter $d_1$ at which the fiber's core will break.

A failure or a break of the fiber's core is determined automatically by the aforedescribed elements in accordance with a labor-saving procedure. High intensity light from helium-neon laser 14 is focused via coupler 15 into the launch end 11a′ of length 11a of optical fiber. Since the launch end of the fiber actually is fed through the center of supply spool 12 in such a manner so as not to move when the spool turns, light continues to pass through the length of optical fiber 11 as a portion of the fiber is fed into jaw mechanism 20.

Some light is scattered (cladding and radiation modes) within light-tight enclosure 20. A minimum threshold signal is established to account for noise, light leakage of the enclosure and normally scattered light from the unbroken fiber. Also, prior to when a break occurs, a certain amount of the light from the helium-neon laser is scattered from the fiber because of the fiber's bending before fracture. However, since the inner walls of the enclosure absorb light, this small amount of scattered light does not actuate sensor 33 and cause false indications of fiber break. To discriminate against these levels of scattering which might give false indications of failure, either detector 33 or amplifier 34 has a threshold circuit to measure only photo currents above a preset level which is determined from calibration with sample fibers.

When, however, portion 11b fails at a break 11c, there is such an increase in the light intensity within enclosure 30 that the photo detector of sensor 33 detects this light and produces a current that is amplified by amplifier 34. Controller 40 receiving this signal provides the appropriate signals for the motor-driven supply spool 12 and take-up reel 13 to advance fiber 11 in incremental lengths $l_0$ so that another measurement to failure of the fiber can be reinitiated. The portion of optical fiber 11 that has been previously broken advances onto take-up reel 13 because the buffer or polymer overcoating remains sufficiently intact to continue the feeding of the fiber. Normally, no further manual feeding is required, only at the initial set-up and calibration.

Each time the fiber fails, the diameter $d_1$ is recorded by recorder 45 since controller 40 provides an indication of how far the motor-drive mechanism 23 has advanced. At the conclusion of a predetermined number of discrete measurements an indication of the failure probability is thereby provided from a series of failure stress indications and may be outputed in document or in proper format for recorder 45.

Referring once again to FIGS. 2 and 3, block 22 of jaw mechanism 20 is suitably connected to motorized stage 23 so that only block 22 moves with respect to block 21. This reciprocable motion of the moveable L-shaped block is in accordance with predetermined signals coming from controller 40. When the L-blocks are separated from each other a predetermined distance, fiber 11 is fed into the mechanism by drum 12 and reel 13. Roller bearing 23d receives driving signals from controller 40 and pushes the fiber downwardly between blocks 21 and 22 to the position 23d′ shown in phantom in FIG. 3 to form a loop 11b. Two smooth and rounded bearing surfaces 26 and 27 help direct fiber 11 in and out of between the blocks. The volume around the surfaces are of a material, such as Teflon, which doesn't damage or create defects in the fiber or buffer. After the loop is shaped and fitted into grooves 21a and 22a, the roller bearing is withdrawn to stay out of the pathway of the moving L-shaped block. Moveable L-shaped block 22 is advanced until loop 11b fails at break 11c. When sensor 33 detects a failure, block 22 is withdrawn by motor 23b of motorized stage 23 and the cycle can be repeated.

This concept provides for an automatic method of measuring the strength of a long length of optical fiber. It efficiently streamlines strength measurements without having to cut samples, insert them in a tensile test machine and to manually collect strength and failure data. The interfacing with a computer-controller realizes a complete data acquisition system with minimum operator interface and a reduced labor intensity.

The L-blocks optionally are driven by continuous motors or step motors. Step motors have the advantage of superior calibration, adaptability to control and reduction of back flash which could lead to measurement errors. The use of a light-guiding-and-scattering-on-breakage approach provides a means to exactly to determine loop diameter at breakage and hence the fracture strength of a particular fiber.

The system as described is first calibrated to precisely measure the breakage or failure loop diameter $d_1$. This is done by noting that the fiber, when looped, has the greatest stress on the outer surface of the glass while the inner part of the loop is in compression. The calibration may be performed in several ways but what is measured is the spacing $d+(2)(t)$ where t is this thickness of the buffer or polymer overcoating. The spacing between the jaws of the L-blocks is calibrated together with the step motor to relate number of the motor steps with the actual spacing $\Delta$.

During the ith cycle of measurement, the fiber will fail at a jaw separation $\Delta_i$. The computer-controller records $\Delta_i$ and the cycle is repeated. After the length of fiber is measured, the computer, after appropriate programming, subtracts the thickness of the fiber to arrive at the correct loop diameter $d_1$ at which breakage or failure occurs, $d_1 = \Delta_i - 2t$. Thence, the stress at failure is calculated, $\sigma_i = 2E\rho/d_i$.

The probability of failures are estimated using the approximate equation, $\rho_j = j/n+1$, where j is the jth measurement of n cycles. Next, the n measurements are ordered from lowest to highest stress and paired with a probability $\rho_j$ so that the lowest failure stress is correlated with the probability $1/n+1$ and the highest with $n/n+1$. This ordering is effected by means of a sorting utility as part of the process control software. From the foregoing the Weibull distribution is fitted to the data using equation (1). For convenience, this equation is linearized by taking logarithms;

$$\ln \ln \left( \frac{1}{F_i + 1} \right) = M \ln \left( \frac{\sigma_i - \sigma_p}{\sigma_o - \sigma_p} \right)$$

Since the stepping motor rate is selectable, the stress rate $\sigma_f$ also is selectable for computation. These data also may be used in the fracture mechanics models to compute the parameters, such as the fatigue susceptibility factor, N, and others, to make long-term life predictions. In the simplest embodiment of the fracture mechanics relationships, the stressing rate is related to failure probability F, Weibull slope, m, and fatigue parameters B, N, and $S_o$ through the equation:

$$\ln S = 1/N + 1\{\ln B + \ln(N+1) + (N-2)(1/m \ln\ln(1/1-F) + \ln S_o) + \ln \sigma\}$$

where S is strength of fiber at failure, see the article by J. Ritter et al. "Statistical Reproducibility of the Crack Propagation Parameter N in Dynamic Fatigue Tests" appearing in *J. Am. Ceramics Soc.* 62, pp. 542–543, (1979). In fitting this data, the conventional least squares technique is used to obtain the "best" fit. The least squares method minimizes the sum of the departures from an idealized function. The method is well known to practicing scientists and engineers and is widely discussed in books on statistics and in the treatment of experimental data.

Obviously, many modifications and variations of the present invention are possible in the light of the above teachings. It is therefore to be understood that within the scope of the appended claims the invention may be practiced otherwise than as specifically described.

I claim:

1. An apparatus for rapidly and automatically measuring the strength distribution in an optical fiber having a core for transmitting light comprising:
   means optically coupled to said optical fiber for projecting light longitudinally into said core;
   means disposed adjacent said optical fiber for sensing light emanating from breaks in portions of said core;
   means disposed to receive said optical fiber therein for initiating said breaks in said fiber;
   means connected to said optical fiber for feeding said portions of said optical fiber through the initiating means; and
   means operatively connected to the light sensing means, the initiating means and the feeding means for actuating the automatic feeding of said portions by said feeding means and the initiating of said breaks in said optical fiber by said initiating means in response to the sensing of said light emanating from each of said breaks in said fiber.

2. An apparatus according to claim 1 further including:
   a light absorptive enclosure containing said light sensing means and said initiating means.

3. An apparatus according to claim 2 in which said initiating means includes a jaw mechanism having a fixed L-shaped block and a moveable L-shaped block connected to a motor-driven screw that is driven by the actuating means.

4. An apparatus according to claim 3 in which said initiating means includes a vertically displacable roller sized to fit between the blocks to form a U-shaped in the optical fiber after said feeding means places said portion of said optical fiber therein.

5. An apparatus according to claim 4 in which said blocks each include a groove to receive and shape said optical fiber into the U-shaped configuration and a pair of guide rollers to help direct Said optical fiber into the jaw mechanism.

6. A method for rapidly and automatically measuring the strength distribution in an optical fiber having a core for transmitting light comprising:
   projecting light longitudinally into said core;
   feeding portions of said optical fiber through a jaw mechanism;
   initiating breaks in said optical fiber in said jaw mechanism;
   sensing light emanating from breaks in portions of said core of said optical fiber with a photodetector; and
   actuating the automatic feeding of said portions and the initiating of said breaks in said optical fiber by said jaw mechanism in response to the sensing of said light emanating from each of said breaks in said core.

7. A method according to claim 6 further including:
   containing said photodetector and said jaw mechanism in a light-tight and light absorptive enclosure.

8. A method according to claim 7 in which the step of initiating includes the forming of a U-shape of said portion of said optical fiber between blocks with a vertically displacable roller prior to the step of feeding.

* * * * *